(12) United States Patent
Kung et al.

(10) Patent No.: US 8,657,875 B2
(45) Date of Patent: Feb. 25, 2014

(54) METHOD AND APPARATUS FOR PUMPING BLOOD

(75) Inventors: Robert T. V. Kung, Andover, MA (US); Farhad Zarinetchi, Chelmsford, MA (US); Robert M. Hart, Arlington, MA (US)

(73) Assignee: Abiomed, Inc., Danvers, MA (US)

( * ) Notice: Subject to any disclaimer, the term of this patent is extended or adjusted under 35 U.S.C. 154(b) by 612 days.

(21) Appl. No.: 11/235,691

(22) Filed: Sep. 26, 2005

(65) Prior Publication Data
US 2007/0073393 A1    Mar. 29, 2007

(51) Int. Cl.
*A61M 1/10*    (2006.01)
(52) U.S. Cl.
USPC ............ 623/3.13; 623/3.28; 623/3.1; 600/17; 417/14
(58) Field of Classification Search
USPC ............... 623/3.1, 3.13, 3.24–3.25, 3.28, 3.3; 600/17; 604/6.11
See application file for complete search history.

(56) References Cited

U.S. PATENT DOCUMENTS

| | | | |
|---|---|---|---|
| 4,369,530 A | | 1/1983 | Robinson et al. |
| 4,376,312 A | | 3/1983 | Robinson et al. |
| 4,397,049 A | * | 8/1983 | Robinson et al. ............ 623/3.25 |
| 4,588,404 A | | 5/1986 | Lapeyre |
| 4,662,358 A | | 5/1987 | Farrar et al. |
| 4,888,011 A | | 12/1989 | Kung et al. |
| 4,976,729 A | | 12/1990 | Holfert et al. |
| 5,017,103 A | | 5/1991 | Dahl |
| 5,084,064 A | | 1/1992 | Barak et al. |
| 5,147,388 A | | 9/1992 | Yamazaki |
| 5,263,979 A | | 11/1993 | Isoyama et al. |
| 5,352,180 A | * | 10/1994 | Candelon et al. ............... 600/17 |
| 5,888,242 A | | 3/1999 | Antaki et al. |
| 5,895,421 A | | 4/1999 | Nakhmanson |

(Continued)

FOREIGN PATENT DOCUMENTS

| | | |
|---|---|---|
| WO | WO 97/42413 | 11/1997 |
| WO | WO 00/07643 | 2/2000 |

OTHER PUBLICATIONS

Bullister et al., "Physiologic Control Algorithms for Rotary Blood Pumps using Pressure Sensor Input," Artif Organs, vol. 26, No. 11, 2002, pp. 931-938.

(Continued)

*Primary Examiner* — David Isabella
*Assistant Examiner* — Suba Ganesan
(74) *Attorney, Agent, or Firm* — Foley & Lardner LLP

(57) ABSTRACT

At least one aspect is directed to a totally artificial heart, and at least another aspect is directed to a method of controlling blood flow in a patient. The totally artificial heart may include a first rotary pump having an input to receive blood and an output to provide blood to a patient's lungs, a second rotary pump having an input to receive blood and an output to provide blood to the patient's body, a first sensor associated with the first rotary pump, a second sensor associated with the second rotary pump, and a control system coupled to the first sensor, the second sensor, the first rotary pump and the second rotary pump and configured to control characteristics of the first rotary pump and the second rotary pump based on signals received from at least one of the first sensor and the second sensor such that an average flow of blood through the second rotary pump is greater than an average flow of blood through the first rotary pump.

9 Claims, 11 Drawing Sheets

(56) References Cited

U.S. PATENT DOCUMENTS

| | | | |
|---|---|---|---|
| 5,980,571 A | 11/1999 | Nomura et al. | |
| 6,015,434 A | 1/2000 | Yamane | |
| 6,048,363 A * | 4/2000 | Nagyszalanczy et al. | ... 623/3.13 |
| 6,066,086 A | 5/2000 | Antaki et al. | |
| 6,071,093 A | 6/2000 | Hart | |
| 6,179,773 B1 | 1/2001 | Prem et al. | |
| 6,368,080 B1 * | 4/2002 | Sipin | ............... 417/415 |
| 6,422,990 B1 | 7/2002 | Prem | |
| 6,443,983 B1 | 9/2002 | Nagyszalanczy et al. | |
| 6,527,698 B1 * | 3/2003 | Kung et al. | ............... 600/16 |
| 6,540,658 B1 * | 4/2003 | Fasciano et al. | ......... 623/3.21 |
| 6,623,420 B2 | 9/2003 | Reich et al. | |
| 6,817,836 B2 * | 11/2004 | Nose et al. | ......... 623/3.24 |
| 7,238,165 B2 * | 7/2007 | Vincent et al. | ......... 623/3.11 |
| 2002/0147495 A1 | 10/2002 | Petroff | |
| 2004/0039243 A1 | 2/2004 | Bearnson et al. | |
| 2004/0152944 A1 | 8/2004 | Medvedev et al. | |
| 2005/0014991 A1 | 1/2005 | Sugiura | |
| 2005/0071001 A1 | 3/2005 | Jarvik | |
| 2005/0107658 A1 | 5/2005 | Brockway | |

OTHER PUBLICATIONS

Endo et al., "Control Strategy for Biventricular Assistance with Mixed-Flow Pumps," Artif Organs, vol. 24, No. 8, 2000, pp. 594-599.

Kung et al., "Design Considerations for Bearingless Rotary Pumps," Artif Organs, vol. 21, No. 7, 1997, pp. 645-650.

Saxon, Jr. et al., "An Ideal Heart Pump with Hydrodynamic Characteristics Analogous to the Mammalian Heart," Transaction Am. Soc. Artif Organs, Apr. 10-11, 1960; 6: 288-291.

Qian et al., "Measurement of rotary pump flow and pressure by computation of driving motor power and speed," Journal of Medical Engineering & Technology, vol. 24, No. 6, (Nov./Dec. 2000), pp. 273-276.

Frazier et al., "Total Heart Replacement with Dual Centrifugal Ventricular Assist Devices," Asaio J., (May-Jun. 2005), 52(3):224-229.

Tuzun, E., "Total Heart Replacement with Dual Centrifugal Cardiac Assist Devices," Oral Papers held at the Heart Failure and Rotary Blood Pump Summit, Oct. 7-10, 2004, InterContinental Hotel and MBNA Conference Center, Cleveland, Ohio, pp. 1.

Yomoyuki, Y., "Development of Automatic Control System with Nano Sensors for Rotary Blood Pump Total Artificial Heart," Oral Papers held at the Heart Failure and Rotary Blood Pump Summit, Oct. 7-10, 2004, InterContinental Hotel and MBNA Conference Center, Cleveland, Ohio, pp. 1.

Invitation to Pay Additional Fees with Partial International Search Report for PCT/US2006/037370 mailed Mar. 1, 2007.

International Search Report for PCT/US2006/037370 mailed May 16, 2007.

Frazier, O.H. et al., "Total Heart Replacement Using Dual Intracorporeal Continuous-Flow Pumps in a Chronic Bovine Model: A Feasibility Study", ASAIO Journal 2006, pp. 145-149. Submitted for consideration Jun. 2005.

Nosé, Y., "Can We Development a Totally Implantable Rotary Blood Pump?", Artificial Organs, 19(7): 561-562, Blackwell Science, Inc., Boston, 1995 International Society for Artificial Organs.

* cited by examiner

METHOD AND APPARATUS FOR PUMPING BLOOD

BACKGROUND OF INVENTION

1. Field of Invention

Embodiments of the invention relate generally to, but are not limited to, systems and methods for pumping blood through the body, and more particularly, at least one embodiment is directed to a totally artificial heart and method of controlling the artificial heart, while other embodiments may be directed to devices and methods for assisting the operation of a patient's heart.

2. Discussion of Related Art

Total artificial hearts (TAH) utilizing positive displacement pumps have been successfully used to replace the functions of the human heart. See, for example, U.S. Pat. No. 4,888,011 to Kung et al. entitled "Artificial Heart" (incorporated herein by reference in its entirety). Such pumps utilize an alternating left-right pumping device with left and right pumping chambers, each including a membrane or diaphragm separating the chamber into a blood flow section and a hydraulic section. During left-side blood pump ejection, hydraulic fluid is pumped from the right hydraulic section through a hydraulic pump into the left hydraulic section, hereby expanding the left side membrane into the left blood pumping section to forcibly eject blood in the section. At the same time, removal of hydraulic fluid from the right side hydraulic section causes the right side membrane to contract, resulting in concurrent filling of the right side blood pump while left side ejection is taking place. To maintain physiologic right atrium pressure (RAP) and left atrium pressure (LAP) a separate hydraulic chamber is used to derate the right side stroke volume. The hydraulic flow is reversed for right side ejection and left side filling.

As is known, the volume of blood flow pumped by the left side of the heart is typically higher than that pumped by the right side of the heart. In one type of prior art artificial heart, to compensate for this imbalance, an atrial shunt is provided between the left atrium and the right atrium. While the use of the shunt may help to compensate for the imbalance, this scheme allows mixing of oxygenated blood with deoxygenated blood reducing the efficiency of oxygenation under certain physiologic circumstances.

While positive displacement pumps have been successful in mimicking the functions of the human heart, a number of difficulties associated with the use of these devices has prevented wide spread use. For example, positive displacement pumps currently in use tend to be too large in size to be used in patients with smaller thoracic cavities. In order to mimic physiologic pressures and beat rates, stroke volumes in the range of 50 to 100 cc are typically needed for the left and right ventricle. Thus, using typical existing devices, the pumping chambers must be large enough to pump this volume of blood in a single beat. In addition, an energy converter is typically used to drive the hydraulic fluid between the left and right chambers, thereby increasing the overall size of the device. As a result, such systems normally have a total volume in the range of 700 to 800 cc in order to provide an output of up to 8 L/min. Moreover, positive displacement pumps typically require the use of artificial valves in order to pump blood from the pumping chambers in a unidirectional manner.

One alternative approach to using positive displacement pumps is to use rotary pumps, which pump blood directly, rather than by displacement. These rotary pumps, which generally include axial and centrifugal flow pumps, can be operated in either steady or pulsatile flow modes, and do not require a stroke volume to be the determining factor with respect to the size of the system. By controlling the rotary pump rotor speed, pulsatile flow can be delivered from these pumps at physiologic volumes and pressures with system sizes not significantly larger than the stroke volumes delivered.

An example rotary pump of the centrifugal type is disclosed in U.S. Pat. No. 5,017,103 to Dahl entitled "Centrifugal Blood Pump and Magnetic Coupling" (which is hereby incorporated by reference). This pump has a broad, relatively flat impeller situated within a housing that has inlet and outlet tube connector ports. Another exemplary rotary pump is disclosed in U.S. Pat. No. 6,071,093 to Hart et al., entitled "Bearingless Blood Pump and Electronic Drive System" (which is hereby incorporated by reference). Hart discloses a rotary pump having a magnetically and/or hydrostatically suspended rotor.

While rotary pumps have the advantage of mechanical simplicity and small size, a number of issues must still be resolved before such pumps can be used in a total artificial heart. Among the issues that need to be addressed are control strategies that allow the pumps to respond to varying physiological demand, and that accommodate the natural flow imbalance between the pulmonary and systemic circulations.

SUMMARY OF INVENTION

At least some embodiments of the invention are directed to systems and methods for pumping blood through the body. In particular, one or more embodiments are directed to a replacement heart, control systems and methods for controlling replacement hearts and ventricular assist devices.

A first aspect of the invention is directed to a replacement heart. The replacement heart includes a first rotary pump having an input to receive blood from the patient's body and an output to provide blood to a patient's lungs, a second rotary pump having an input to receive blood from the lungs and an output to provide blood to the patient's body, a first sensor associated with the first rotary pump, a second sensor associated with the second rotary pump, and a control system coupled to the first sensor, the second sensor, the first rotary pump and the second rotary pump and configured to control characteristics of the first rotary pump and the second rotary pump based on signals received from at least one of the first sensor and the second sensor such that an average flow of blood through the second rotary pump is greater than an average flow of blood through the first rotary pump.

In the artificial heart, the first sensor may be configured to detect a first pressure at the input of the first rotary pump, and the second sensor may be configured to detect a second pressure at the input of the second rotary pump, and the control system may be configured to control a speed of the first rotary pump based on the first pressure and a speed of the second rotary pump based on the second pressure. In another version, the first sensor may be configured to detect a first pressure at the input of the first rotary pump, and the second sensor may be configured to detect a second pressure at the input of the second rotary pump, and the control system may be configured to control a speed of the second rotary pump based on the first pressure and to control a speed of the first rotary pump based on the second pressure. The speed of the first rotary pump may be controlled in an inverse manner with changes in the second pressure.

In another version of the first aspect, the first sensor may be configured to detect a first pressure at the input of the first rotary pump, and the second sensor may be configured to detect a second pressure at the input of the second rotary pump, the control system may be configured to determine a first blood flow through the first rotary pump and a second blood flow through the second rotary pump, and the control system may be configured to control a speed of at least one of the first rotary pump and the second rotary pump based on at least one of the first blood flow and the second blood flow.

In still another version, the second sensor may be configured to detect a second pressure at the input of the second rotary pump; and the control system may be configured to set a target pressure level of the second sensor based on a speed of the second rotary pump at which the second pressure approaches a threshold value. The control system may be configured to adjust the speed of the second rotary pump based on changes in the second pressure from the target pressure level. The first sensor may be configured to detect a first pressure at the input of the first rotary pump, wherein the control system is configured to set a target pressure level of the first sensor based on a speed of the first rotary pump at which the first pressure approaches a threshold value.

In another version of the first aspect of the invention, each of the first sensor and the second sensor may be configured and controlled to determine at least one characteristic associated with the filling of one of the patient's left atrium and the patient's right atrium. Further, the control system may be configured to control each of the first rotary pump and the second rotary pump to operate in a pulsatile mode of operation. Further, the control system may be configured to control at least one of speed and power usage of the first rotary pump and the second rotary pump, and the control system may be configured to dither at least one of the speed and the power usage of at least one of the first rotary pump and the second rotary pump to determine a blood flow through the at least one of the first rotary pump and the second rotary pump.

A second aspect of the invention is directed to a replacement heart. The replacement heart includes a first rotary pump having an input to receive blood and an output to provide blood to a patient's lungs, a second rotary pump having an input to receive blood and an output to provide blood to the patient's body, and a control system coupled to the first rotary pump and the second rotary pump and configured to determine a first blood flow through the first rotary pump and a second blood flow through the second rotary pump and to control operation of the first rotary pump and the second rotary pump based on the first blood flow and the second blood flow while maintaining a difference between the first blood flow and the second blood flow.

The control system may be configured to control the second rotary pump by increasing a speed of the second rotary pump until a drop in the second blood flow is detected. The control system may be configured to control the first rotary pump by increasing a speed of the first rotary pump until a drop in the first blood flow is detected. The control system may be configured such that at least one of the first blood flow and the second blood flow is determined by dithering at least one of speed and power usage of at least one of the first rotary pump and the second rotary pump.

A third aspect of the invention is directed to a method of controlling a dual rotary blood pump having a first pump to provide blood flow to a patient's lungs and a second pump to provide blood flow to the patient's body. The method includes detecting a first characteristic related to blood level of the patient's left atrium, detecting a second characteristic related to blood level of the patient's right atrium, and controlling operation of the first pump and the second pump based on the first characteristic and the second characteristic to maintain blood flow in the body such that an average flow of blood through the second pump is greater than an average flow of blood through the first pump.

In the method, the first characteristic may be related to right atrial pressure, and the second characteristic may be related to left atrial pressure, and the method may further include controlling a speed of the first pump based on the right atrial pressure and a speed of the second pump based on the left atrial pressure. In another version, the method further includes controlling a speed of the first pump based on the left atrial pressure and a speed of the second pump based on the right atrial pressure, with the speed of the first pump controlled in an inverse manner with changes in the left atrial pressure. In another version, the method further includes detecting blood flow through the first pump, detecting blood flow through the second pump, and controlling a speed of at least one of the first pump and the second pump based on at least one of the first blood flow and the second blood flow. In still another version, the method may include setting a target pressure level for the left atrial pressure based on a speed of the second pump at which the left atrial pressure approaches a threshold value. The method may include adjusting the speed of the second pump based on changes in the left atrial pressure from the target pressure level, and setting a target pressure level of the right atrial pressure based on a speed of the first pump at which the right atrial pressure approaches a threshold value. The method may also include controlling each of the first pump and the second pump to operate in a pulsatile mode of operation. The method may further include determining blood flow through at least one of the first pump and the second pump by dithering at least one of speed and power usage of the at least one of the first pump and the second pump.

A fourth aspect of the invention is directed to a method of controlling a dual rotary blood pump having a first pump to provide blood flow to a patient's lungs and a second pump to provide blood flow to the patient's body. The method includes determining a first blood flow through the first pump, determining a second blood flow through the second pump, and controlling the first pump and the second pump based on the first blood flow and the second blood flow to maintain a difference between the first blood flow and the second blood flow.

The method may further include increasing the speed of the second blood pump until a drop in the second blood flow is detected, and increasing a speed of the first blood pump until a drop in the first blood flow is detected. In the method, determining the first blood flow may include dithering at least one of speed and power usage of the first pump and determining the second blood flow may include dithering at least one of speed and power usage of the second pump.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
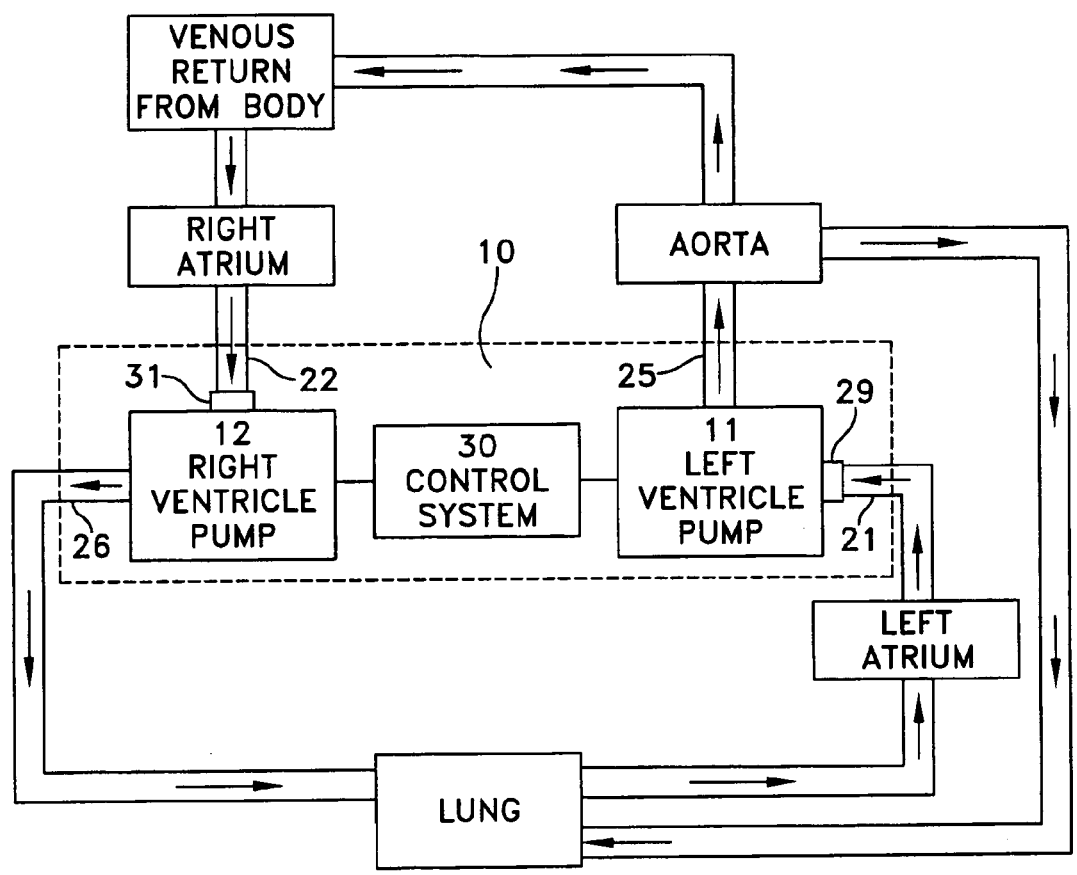
FIG. 1 is a functional block diagram of one embodiment of an artificial heart implanted in a patient.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

As described below, at least some embodiments of the present invention are directed to a totally artificial heart and methods of controlling artificial hearts. Nonetheless, at least some embodiments of the invention or particular aspects of embodiments of the invention may be used with other devices, such as ventricular assist devices (VADs) and with external blood pumps. Further, the use of the term replacement heart in this description and in the claims refers to a total artificial heart as well as a biventricular assist device that may supplement the operation of a native heart.

Left-right cardiac output differences have been well documented. Physiologically, the volume of blood flow pumped by the left side of the heart is higher than that pumped by the right side of the heart. This difference is largely attributable to a circulatory pathway known as the bronchial shunt flow. This flow originates in the left arterial system, passes through the bronchial tissue and then returns directly to the left atrium. This difference typically appears to be about one to fifteen percent of cardiac output with the left side flow always greater than the right side flow. As described below, at least some embodiments of artificial heart systems and control methods disclosed herein provide independent control of a right side pump and a left side pump and account for this inherent physiological circulatory imbalance and provide improvements over prior systems and methods that utilize control schemes based on equal flows in the right side and the left side of an artificial heart. Further, at least some embodiments provide control of a TAH without the use of an atrial shunt.

Blood pressure in the right atrium (RAP or right atrial pressure) of the heart is generally driven by systemic circulatory pressure from the venous return into the heart. Average RAP typically ranges from 3 to 15 mmHg, depending on the physiology of the individual and that individual's current activity level. Average left atrial pressure (LAP) typically ranges from 3 to 20 mmHg. In a biventricular cardiac prosthesis, controlling LAP within a physiological range is important. If LAP is consistently high, excessive fluid build-up and retention in the lungs can cause damage to the lungs. At least some embodiments disclosed herein provide flow balance control in a biventricular cardiac prosthesis system to maintain LAP within a physiological range.

Further, it is also beneficial to balance flow between the left and right sides of an artificial heart to maintain LAP within a physiological range and to allow RAP to respond to physiological demands. In prior devices, direct measurement of LAP or RAP, however, is problematic because it generally involves placement of a conventional pressure transducer directly in contact with blood flowing through the atrium, with the attendant potential problems of reliability and thrombogenesis. At least some embodiments of the present invention provide improved techniques for measurement of LAP and RAP as well as control schemes for an artificial heart that do not rely solely on direct measurements of LAP and RAP. Further, at least some embodiments utilize characteristics of motors associated with rotary pumps to indirectly determine pressure, allowing some embodiments to operate without pressure sensors, and allowing other embodiments to operate with less accurate pressure sensors, which may or may not contact blood directly.

At least one embodiment of the present invention, which will now be described, provides a cardiac prosthesis, or total artificial heart, capable of responding to varying physiological demands of the body, and having mechanisms for accommodating the natural flow imbalance between the pulmonary and systemic circulations while using minimal blood contacting instrumentation. While at least one embodiment discussed below includes centrifugal pumps, principles of embodiments of the invention may be used with a variety of different style pumps including axial flow pumps and other rotary or non-rotary pumps.

Figure 2A:
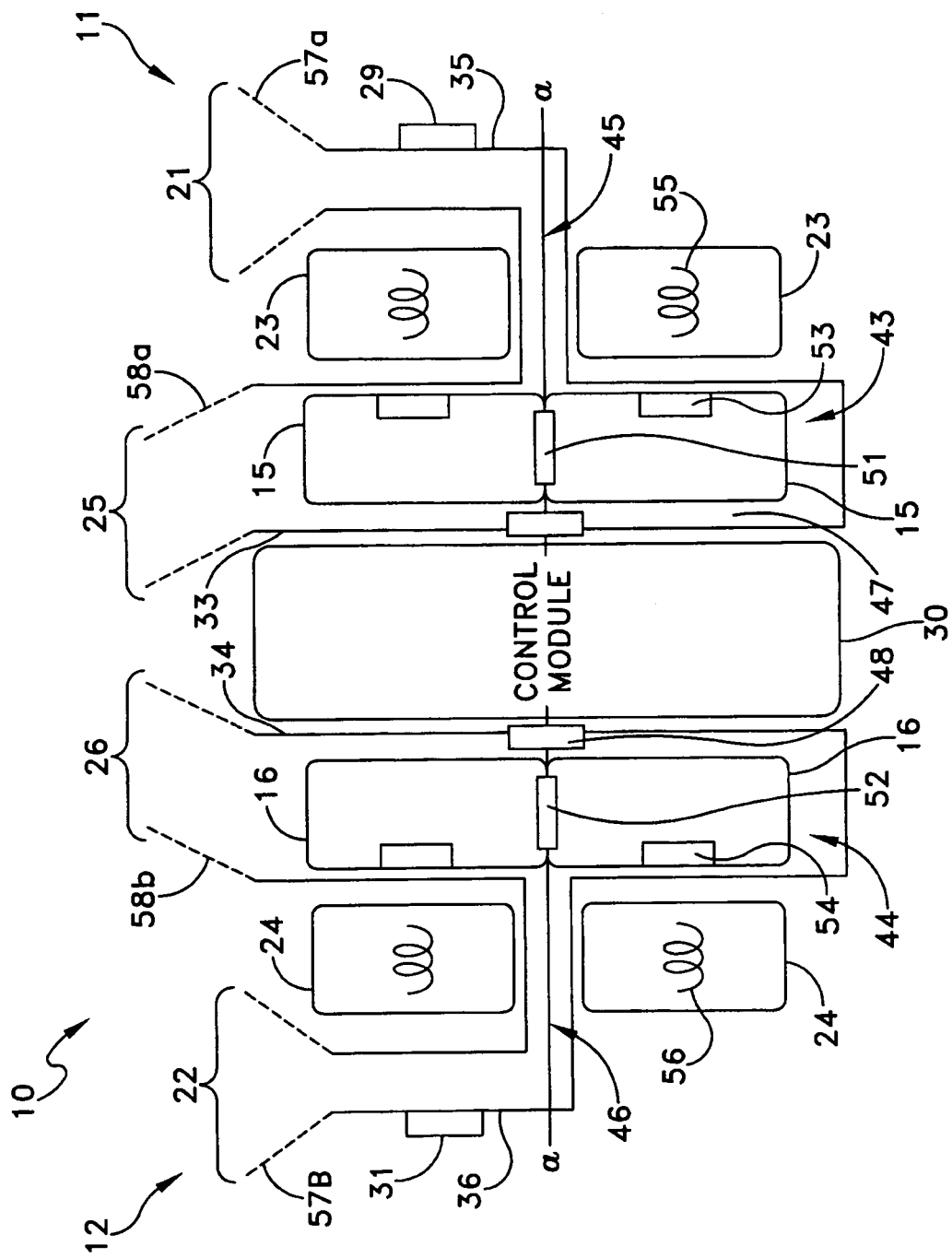
FIG. 2A is a diagrammatic cross-sectional view of an artificial heart in accordance with one embodiment of the present invention.
Figure 2B:
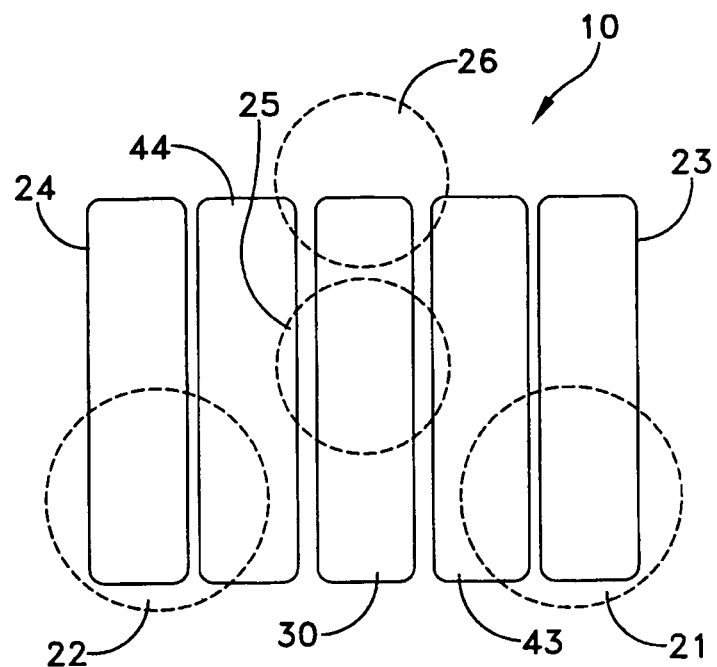
FIG. 2B is a diagrammatic top view of the artificial heart of FIG. 2A.

FIG. 1 illustrates a block diagram of an artificial heart system 10 implanted within a patient in accordance with one embodiment of the invention, FIG. 2A shows a diagrammatic cross-sectional side view of the artificial heart system 10, and FIG. 2B shows a diagrammatic top view. In this embodiment, the system includes left and right blood pumps 11, 12 connected to a control module 30. The left side pump 11 includes a blood input port 21 from the left atrium and a blood output port 25 to the aorta. A left sensor 29 for detecting left atrial pressure (LAP) is positioned at the input port 21 of the left pump 11. The right side pump 12 is constructed similarly to the left side pump 11 and is coupled to the right atrium at a blood input port 22 and the pulmonary artery at a blood output port 26. A right sensor 31 for detecting right atrial pressure (RAP) is positioned at the input port 22 of the right pump 12. In the embodiment shown, the control module 30 is positioned between the pumps 11, 12 and is effective to control the pumps 11, 12.

In at least one embodiment, the left and right pumps 11, 12 completely replace the natural ventricles, and the pumps can be attached to atria tissue and vascular tissue using atrial cuffs and vascular grafts respectively. The atrial cuffs and vascular grafts may be sutured to a major vessel and/or to tissue surrounding the vessel or to vestigial atrial tissue following removal of the ventricles to establish a connection for the artificial heart system 10.

As shown in FIG. 2A, an atrial cuff 57a, 57b is provided for suturing the inlet port 21, 22 of each pump 11, 12 to the atrium, and a vascular graft 58a, 58b is provided for suturing the outlet ports 25, 26 to vascular tissue. The cuffs and grafts may be made of a woven or knit polyester or similar plastic type fabric such as, for example, that available under the trade name Dacron®. In at least one embodiment, the atrial cuffs may be implemented using surgical cuffs shown in U.S. Pat. No. 5,084,064, "Surgical Cuff" to Barak et al., which is hereby incorporated herein by reference. A person of ordinary skill in the art will appreciate, based on this disclosure, that other methods for attaching the inlet and outlet ports to vascular tissue can be employed in other embodiments of the present invention.

With further reference to FIG. 2A, the left and right pumps 11, 12 may be implemented using centrifugal blood pumps contained within housings, each of the blood pumps having a rotating impellor or rotor 43, 44, a bearing assembly 47, 48, and stator assemblies 23, 24 having windings 55, 56. Each pump 11, 12 further includes a blood inlet conduit 35, 36, a blood outlet conduit 33, 34, and a blood flow conduit 45, 46 disposed between the blood inlet conduit 35, 36 and the rotors 43, 44. The blood flow conduits 33, 34, 35, 36, 45 and 46 may be implemented using, for example, plastic tubing. As discussed below, in at least one embodiment, the inlet pressure sensors 29, 31 are coupled to, and/or incorporated in the inlet conduits 35, 36.

Each rotor 43, 44 is coupled to one of the blood flow conduits 45, 46 and draws blood in through the inlet conduits 35, 36 and expels blood out through the outlet conduits 33, 34. The rotors 43, 44 include a plurality of impeller blades 15, 16 connected at a central hub 51, 52. A person of ordinary skill in the art will recognize that the number of impellor blades 15, 16, the shape of the impeller blades 15, 16, as well as the connecting features between the impeller blades can be varied in different embodiments of the present invention. The rotors 43, 44 can be connected to and rotate with a shaft about axis a. The shaft interacts with the bearing assembly 47, 48 to allow for relative movement between the rotor 43, 44 and the housing. One example of a pump having rotors arranged in a similar manner is illustrated in U.S. Pat. No. 5,017,103, "Centrifugal Blood Pump and Magnetic Coupling" to Dahl, which is hereby incorporated by reference herein. The rotors 43, 44 can also be suspended within blood flow conduits 45, 46 without using shaft and bearing arrangements as illustrated in U.S. Pat. No. 6,071,093, "Bearingless Blood Pump and Electronic Drive System," to Hart, which is also hereby incorporated by reference herein.

The windings 55, 56 of the stators 23, 24 are coupled to drive electronics contained within the control module 30. The drive electronics provide drive current to the stator windings to drive the rotation of the rotors 43, 44. In the illustrated embodiment, magnets 53, 54 are provided on each impeller and the stator windings 55, 56 fit into space available in the annular region around conduits 45, 46. This motor arrangement is provided for illustrative purposes only, as a person of ordinary skill in the art, based on this disclosure, will be able to vary the motor configuration in a variety of ways. For example, the bearing assemblies 47, 48, may be implemented using a number of different assemblies compatible with mechanical, hydrostatic, magnetic and hydrodynamic support.

The control module 30 is positioned between the two rotors. The control module includes power circuitry, motor driver circuits, sensing circuits and processing circuits. In one embodiment, power is provided for the artificial heart 10 from an external battery pack coupled to the control system 30 through wires that penetrate the skin. In other embodiments, power may be coupled to the artificial heart from an external source using, for example, electromagnetic coupling circuits, and in still other embodiments, the control electronics module may include one or more batteries. The power circuitry is coupled to the power source and provides power at appropriate voltage levels to the other circuits of the control module.

The sensing circuits include a number of interfaces for coupling to sensors in the rotary motors and also includes conditioning circuits for conditioning signals from sensors and for providing the conditioned signals to the processing circuits. The drive circuits provide an electrical interface between the processing circuits and the motors and based on control signals received from the processing circuit provides motor drive signal to the motors.

The processing circuits function as the overall controller of the artificial heart and based on inputs from the sensors determine appropriate control signals to the drive circuits. In one embodiment, the processing circuit may be implemented using a microprocessor, however, in other embodiments discrete logic circuits, programmable gate arrays and/or other circuits may be used to implement control schemes of embodiments of the invention. The processing circuits may include radio frequency transceivers to allow external monitoring and control of the artificial heart.

Still referring to FIGS. 2A and 2B, each pump 11, 12 includes a pressure sensor 29, 31 embedded in the inlet conduits of each pump 11, 12. The pressure sensors 29, 31 are adapted to measure the left and right atrial pressures (LAP and RAP, respectively). The placement of the pressure sensors 29, 31 at the pump inflows allows high shear rates over surfaces that might otherwise be sites for thrombus formation.

Depending on the positions of the pressure sensors 29 and 31, a person having ordinary skill in the art, with the benefit of this disclosure, will appreciate that measurements of pressure at the sensor locations may vary from the LAP and RAP as a result of a pressure drop between the atrium and the inlets of the pump. In embodiments of the present invention, a calibration procedure using actual physiological pressures may be employed to calibrate the pressure sensors to account for any difference between the measured pressure and the actual atrial pressure. Further, in some embodiments of the invention, particularly those used with ventricular assist devices, the pressure sensors may be positioned to measure ventricular pressure rather than atrial pressure.

Figure 2C:
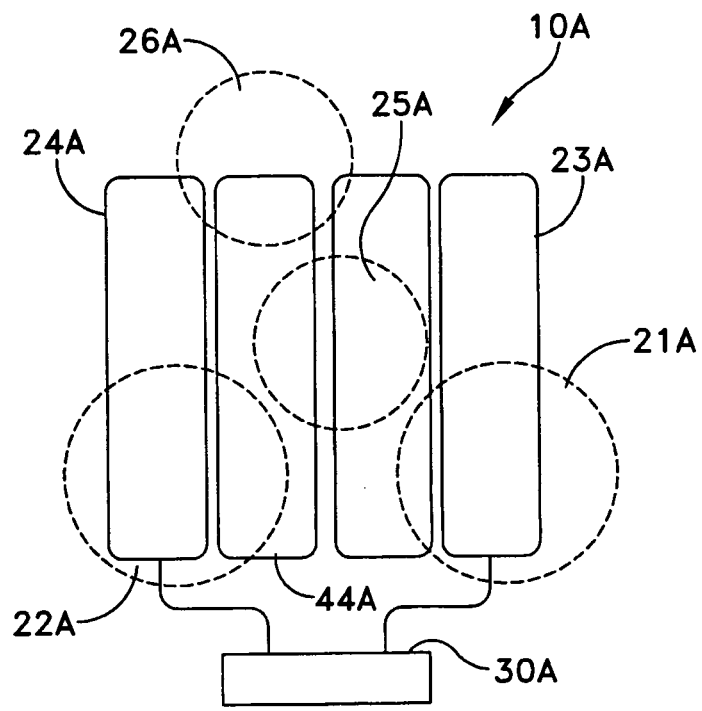
FIG. 2C is a diagrammatic top view of an artificial heart of a second embodiment.

In the embodiment of a TAH discussed above with reference to FIGS. 2A and 2B, the control module 30 is positioned between the two rotary motors. In another embodiment of a TAH 10A, the control module need not be located between the motors. A top view of the TAH 10A is shown in FIG. 2C. Components of the TAH 10A may be the same as or similar to components of the TAH 10, and similar elements are labeled with the same base reference number with an additional suffix "A" added to the components of TAH 10A. As shown in FIG. 2C, the control module 30A is coupled to the motors using cables or wires 27A. The control module 30A may be mechanically coupled to the motors, but need not be. In the TAH 10A, the rotors 43A and 44A may be located adjacent each other with the stators 23A, 24A located adjacent the rotors. The input ports 21A, 22A and the output ports 25A, 26A are positioned adjacent the motors in a manner similar to the ports of TAH 10. TAH 10A operates in a manner similar to TAH 10, and may offer additional advantages by having an overall size and shape that may be more compatible with smaller thoracic cavities.

Different embodiments of control methods for controlling TAH's, such as the artificial hearts 10 and 10A discussed above will now be described. The control methods described herein may be implemented in the processing circuits of the control module 30 in the artificial heart 10. However, as readily understood by those skilled in the art, control methods and apparatus of the present invention are not limited for use with artificial heart 10, but may be used with other TAH, including those that use rotary pumps (eg, axial and centrifugal), positive displacement pumps and other types of pumps, and may be used, for example, with dual rotary devices described in U.S. Pat. No. 6,048,363, "Centrifugal Blood Pump Apparatus," to Nagyszalanczy et al., which is hereby incorporated by reference herein.

Figure 3A:
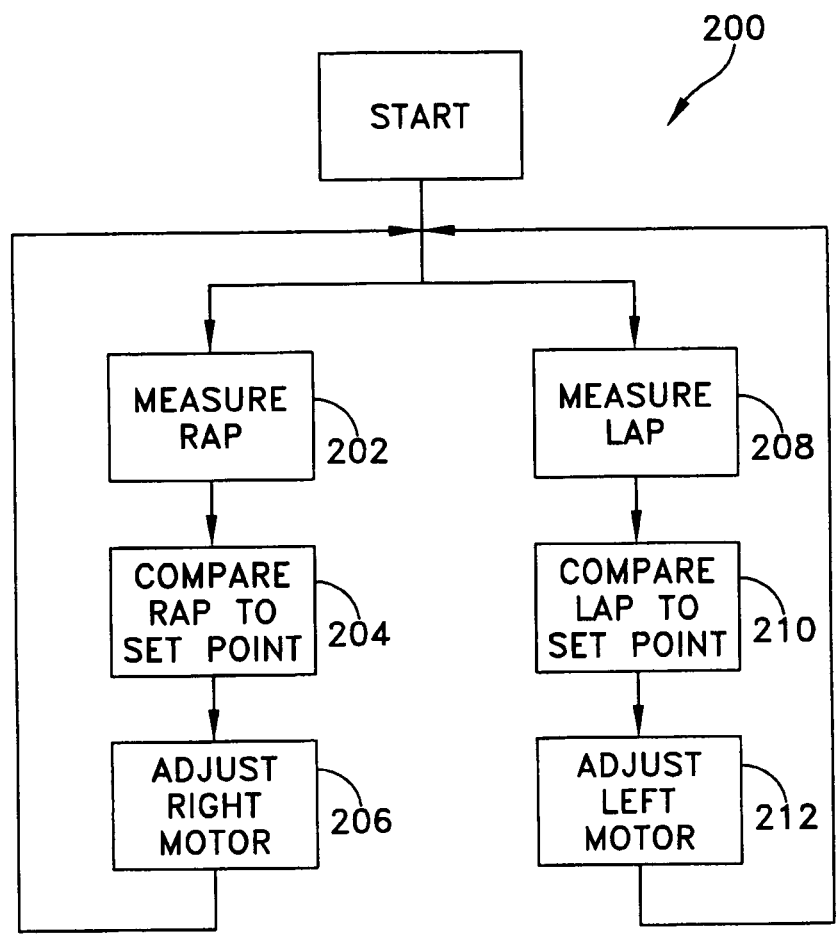
FIGS. 3A, 3B and 3C are flow charts of processes used in embodiments of the invention.

The natural human heart increases cardiac output when the blood-return to the heart increases, a relationship commonly referred to as the Frank-Starling Law. Similarly, in a first control scheme 200 used in at least one embodiment, a control algorithm for a total artificial heart attempts to increase the flow rate of the right pump and the flow rate of the left pump when the right atrial pressure (RAP) increases. The control scheme 200 will be described with reference to FIG. 3A, which shows a flow diagram of the control scheme. Although other factors, such as atrial compliance, influence the relationship between blood-return and RAP, the RAP is one indicator of blood-return to the heart. In one embodiment, the RAP is determined (stage 202), compared to a reference set point (stage 204), and the rotation speed of the right blood pump is adjusted based on the comparison (stage 206). The set point may be, for example, within the range of 3 to 20 mmHg with the particular set point based on the physiology of the individual patient. The particular increments of adjustment may be fixed for a given patient or may be based, in part, on the magnitude of the deviation between the measured RAP and the set point. For higher measured values of RAP the control system gradually increases the pump speed resulting in an increased right pump flow. This results in a reduction of the RAP. Similarly for lower measured values of RAP the control system gradually reduces the pump speed resulting in a decreased right pump flow. This results in an increase in the RAP. In this manner, flow of the right pump is controlled based on RAP.

The flow of the left pump may be controlled in a similar manner based on measured LAP. LAP is measured (stage 208), compared to a set point (stage 210), and the rotation speed of the left blood pump is adjusted based on the comparison (stage 212). The set point for LAP may be the same as the set point for RAP, or in one version, the set point for LAP is set to be approximately double that of RAP to be more consistent with operation of a natural heart. When LAP increases, the left motor speed is increased, when LAP decreases, the left motor speed is decreased. In this control scheme, in response to an increase in the RAP, right flow will be increased causing an increase in the LAP. The increase in LAP will cause an increase in left flow. Accordingly, increases in the RAP cause an increase in both left and right blood flow. In the above-described control scheme, blood flow of both pumps are controlled in a manner that can accommodate differences in flow in the left and right pumps.

In at least one embodiment, adjustments to the speed can be made as often as once every second but not longer than approximately once per minute, which is the blood cycle time through the body, and the magnitude of change is typically 1% to 5% of the operating speed to avoid oscillations, however, in at least one embodiment, the overall operating range of each of the pumps from the lowest speed to the highest speed may be a factor of two.

Figure 3B:
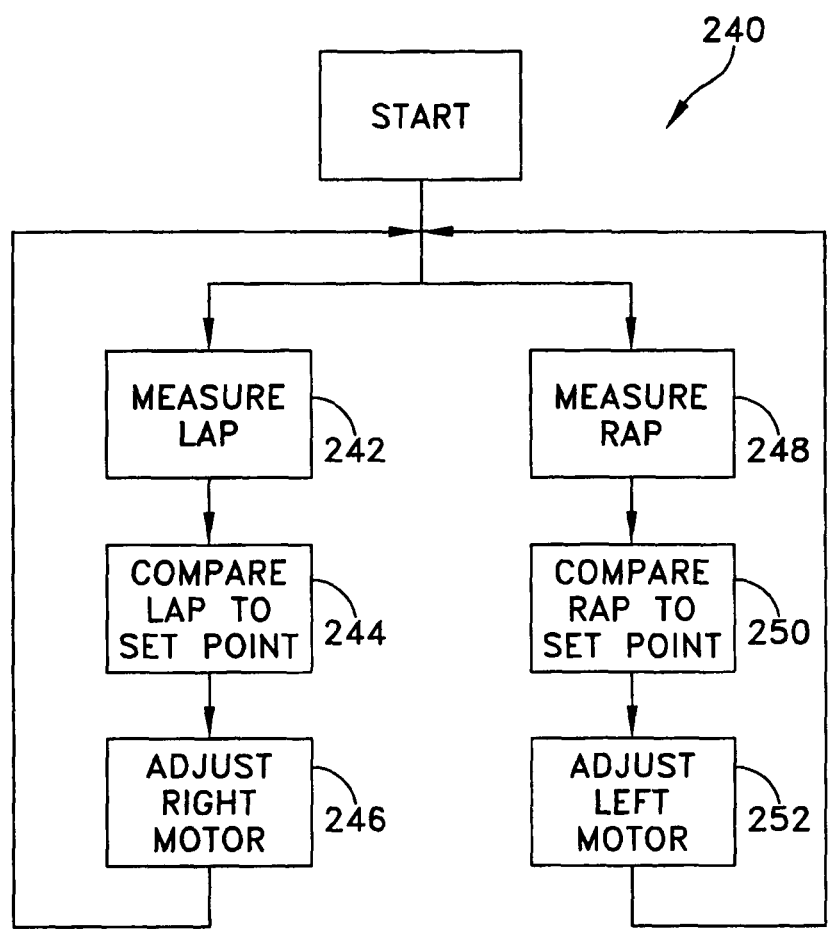

In a second control scheme 240, which will now be described with reference to FIG. 3B, the speed of the left pump is directly controlled based on the RAP. The RAP is measured (stage 248), compared to a set point (stage 250, the set point may be in the range of 3-20 mmHg as discussed above), and based on the comparison, the speed of the left pump is adjusted (stage 252). The speed of the left pump is increased when the RAP is greater than the set point and decreased when the RAP is less than the set point. In this second control scheme, the speed of the right pump is controlled based on measured values of LAP with changes in the speed of the right pump being inversely proportional to changes in the LAP. The LAP is measured (stage 242), compared with a target value (stage 244, for example, 7 mmHg), and based on the comparison, the speed of the right motor is adjusted (stage 246). If the measured LAP is above the target value, then the speed of the right pump is reduced, and if the measured LAP is less than the target value, then the speed of the right pump is increased.

In embodiments described above, control schemes are provided that allow a dual rotary artificial heart to respond to physiologic demand. In another embodiment, which will now be described, improved versions of the first two control schemes described are provided in which the flow rates of the left and right pumps are included in a control algorithm in addition to RAP and LAP. In practice it can be desirable to limit the degree to which the left pump flow can deviate from the right pump flow and the degree to which the right pump flow can approach the left pump flow. This limitation reduces the chance of damage to the lungs caused by an anomalous flow imbalance between the right and left pumps. As is known, because of the bronchial shunt flow phenomenon, the right blood flow does not equal the left blood flow in a natural heart, and the left flow may be 1 to 15% higher than the right blood flow. Similarly, in a third control method of at least one embodiment, the flow rates of the left and right pumps are coupled together in a control algorithm, but not controlled to be equal to each other. The third control method may be used in conjunction with any of the versions of the first and second control methods discussed above.

Figure 3C:
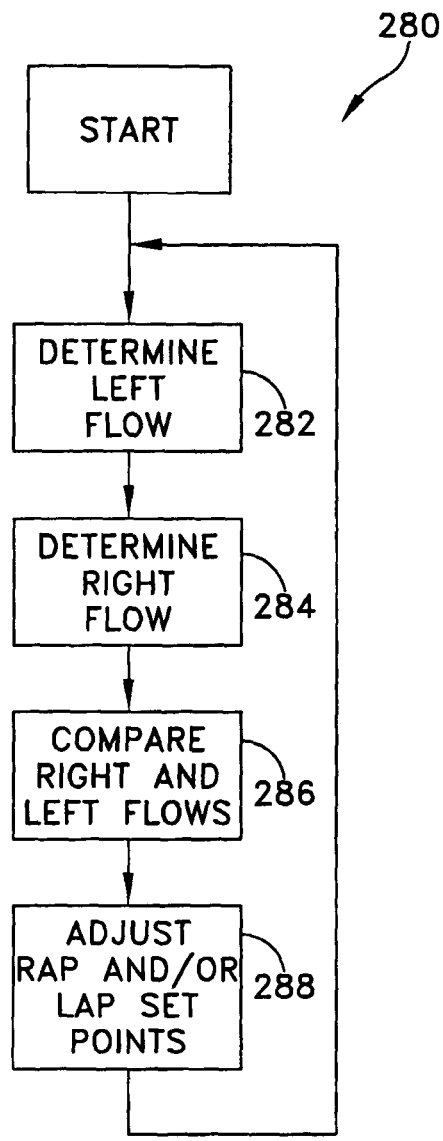

In principle, in this control scheme 280, which will now be described with reference to FIG. 3C, if the right pump flow exceeds that of the left pump by a given margin, the algorithm will change, for example, the RAP set point to limit the right flow. Conversely if the left pump flow exceeds that of the right pump beyond a set margin, the algorithm will adjust, for example, the LAP set point to limit the left flow. Both of these limits will gradually revert to their originally designed values if the right and left flows are within their desired ranges. In the control scheme 280, the left blood flow is determined (stage 282), the right blood flow is determined (stage 284), the left blood flow is compared with the right blood flow (stage 286), and the LAP and/or RAP set points (in control schemes 200 and 240) are adjusted based on the comparison. In particular embodiments, average values of blood flow may be used in the control scheme 280 to prevent frequent adjustments to the set point values for RAP and LAP.

Figure 4:
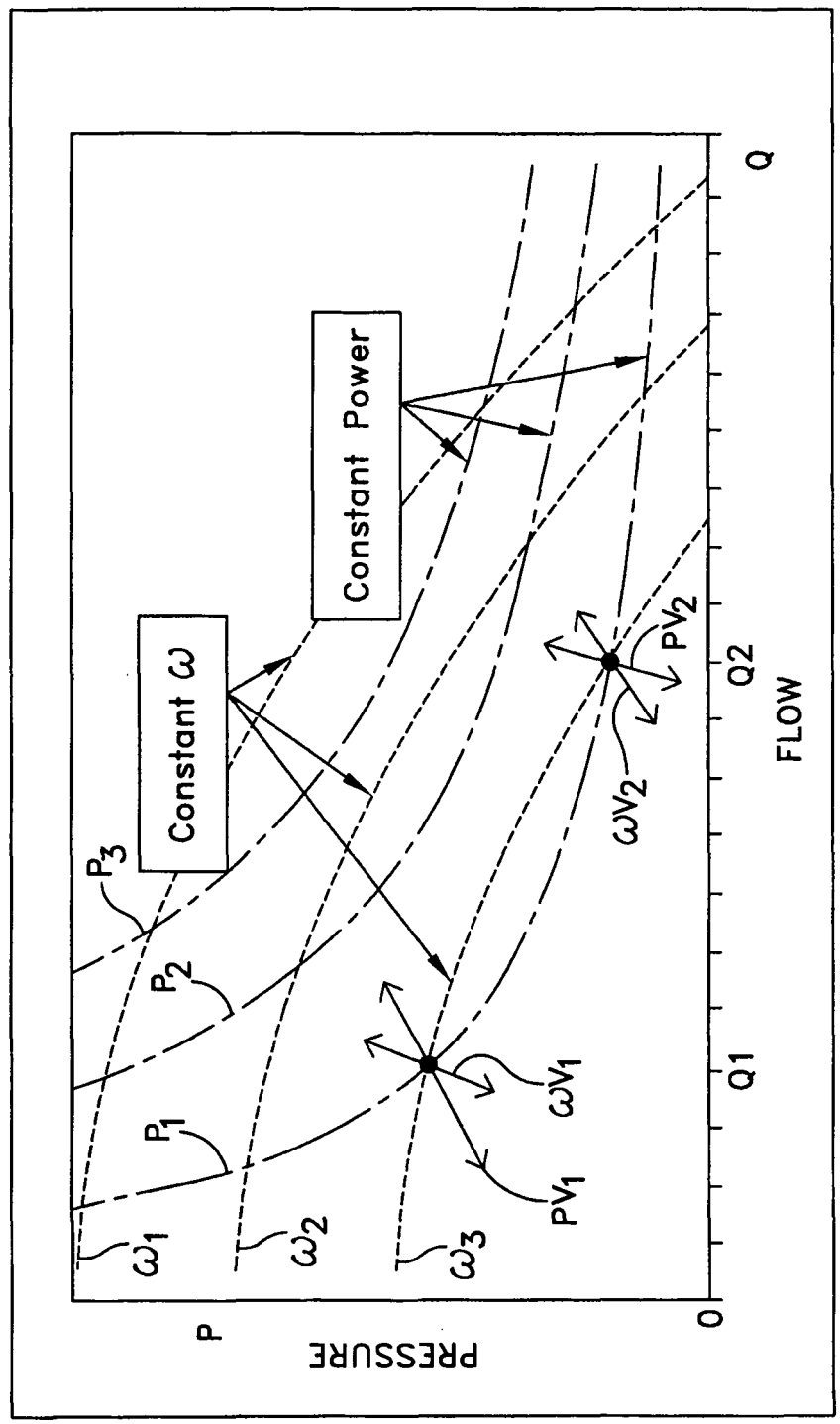
FIG. 4 is a plot showing the relationship between head pressure and flow for different values of rotational speed and input power in typical rotary pumps that may be used in embodiments of the invention.

The flow values required for the above control can be calculated based on readily available motor parameters (speed and power) rather than by providing a flow meter or both upstream and downstream pressure sensors. A pump has two readily observable physical parameters: power consumption P, and rotational speed $\omega$. The pump also has two measurable physical parameters: flow Q, and head pressure p. FIG. 4 illustrates an operational diagram for a typical rotary blood pump. The relationship between head pressure, p (mmHg), versus flow, Q (liters per minute), is shown for a family of constant rotational speeds, $\omega$, (i.e., $\omega1$, $\omega2$, $\omega3$) and for a family of constant power consumption, P, (i.e., P1, P2, P3) used by the pump. For typical rotary pumps, operational graphs like that shown in FIG. 4 are available or may be determined.

In at least one embodiment described above, the speed of the pumps is controlled and is known, and the power to the pumps may be determined based on voltage and current measurements that may be performed within the control module. As shown in FIG. 4, for each set of power and speed values, there are two possible sets of values for flow and head pressure, since the speed and power curves cross at two different points. To determine which of the two flow points is correct, in one embodiment, the current to the motor is varied slightly (dithered) with the voltage kept constant causing a change in power and accordingly a change in speed. The amount by which the speed changes for changes in power provides an indication of the operating parameters of the pump allowing the system to determine which of the two flow values is appropriate. As indicated in FIG. 4, the magnitude of the change in speed with respect to the change in power is different and unique for each pump at the high flow and low flow intersections. For example, with the pump operating at a power of P1 and a speed of w3, the flow will be equal to one of Q1 and Q2. As shown in FIG. 4, if the power is dithered in accordance with either power vector PV1 or PV2 (depending on whether the flow is equal to Q1 or Q2), the speed will change in accordance with either speed vector wV1 or wV2. The operating point can be determined based on the magnitude of the speed vector resulting from dithering the power. Using this dithering approach, the flow can be determined without the use of a flow meter.

Artificial hearts using the control schemes described above may be operated with the pumps in a continuous mode or in a pulsatile mode to be more consistent with the operation of the natural heart. When operated in a continuous mode, typical pump speeds are on the order of 3000 to 8000 rpm to provide typically, five liters per minute of blood flow. When operated in a pulsatile mode, in one embodiment, the pumps are operated at approximately 60 to 120 beats per minute with a duty cycle of approximately 30-50% (for on time or forward flow of the pumps). However, in other embodiments, other beat rates and duty cycles may be used. In the pulsatile mode, typical left pump speed is on the order of 7,000 to 8,000 rpm in the systole portion of the cycle and in the diastole portion, the pumps remain on at a low speed on the order of 3,000 to 4,000 to prevent the possibility of any back flow of blood through the pumps. Typically speeds for the right side are substantially lower, and in one embodiment may be 5,000 to 6,000 rpm for systole and 2,000 to 3,000 during diastole. In pulsatile mode, the speed of the pumps may be controlled to provide the same average speed (and flow) as used in the continuous mode. Further, in controlling pumps in the pulsatile mode in embodiments of the invention, average values of LAP and RAP over systole and diastole may be used. As understood by one of skill in the art, with the use of rotary style pumps, the LAP and RAP will both drop during systole of the pumps (which corresponds to diastole of the atria) and rise during diastole of the pumps (systole of the atria).

In at least one embodiment described above, atrial pressure measurements are used in control schemes for rotary pumps. To accurately control operation using these measurements, it is desirable to use highly accurate pressure sensors that maintain their accuracy over time. In a fourth control scheme 300, which will now be described with reference to FIGS. 5A and 5B, changes in atrial pressure are used in control algorithms rather than absolute pressure measurements. In a calibration mode, a set point is first determined for LAP and RAP, and once the set point is determined changes in pressure from the set point are used to control the speed of the left motor and the right motor.

Figure 5A:
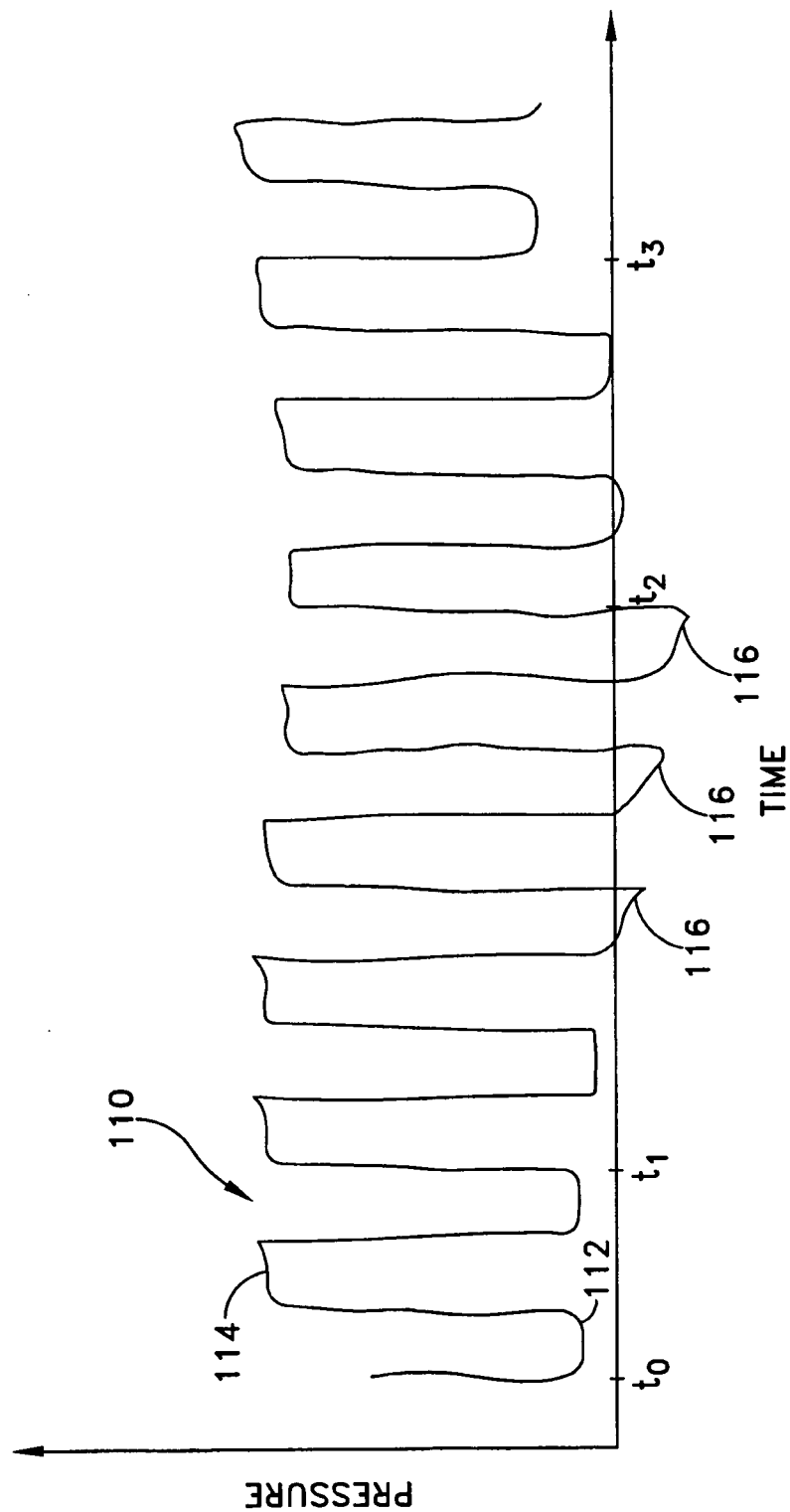
FIG. 5A is a plot of atrial pressures observed in a control scheme of at least one embodiment of the present invention.
Figure 5B:
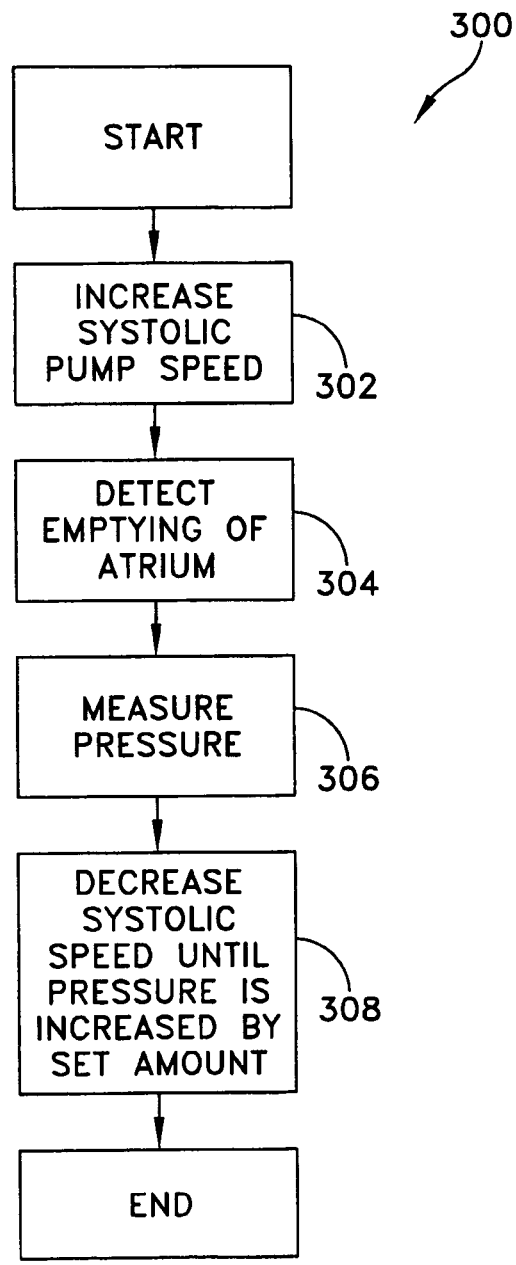
FIG. 5B is a flow chart of a process used in one embodiment of the invention.

As described above, at least some artificial hearts of embodiments of the invention may be operated in a pulsatile mode that simulates the natural beating of the heart. In such a mode of operation, the LAP will drop while the pump is pumping and rise during the off time of the pump. FIG. 5A is a graph showing a curve 110 of LAP verses time for an artificial heart in accordance with one embodiment. At each of the low portions (for example at 112) in the curve, the left motor is on, and at each of the high portions (for example at 114) in the curve, the left motor is running at a slower speed, with no substantial flow. During a calibration routine 300 (see FIG. 5B), starting at time t1, the systolic speed of the left motor is slowly increased (stage 302) until the shape of the pulse in the diastolic portion of the LAP pressure curve starts to show a sharp decrease as shown at points 116 in FIG. 5A. This decrease indicates that the filling pressure is near zero (stage 304). At this point (time t2) the pressure is measured (stage 306) and the speed is slowly decreased until the diastolic portion of the pressure is increased by a set amount (stage 308), which in one embodiment is 10 mmHg. In FIG. 5A, at time t3, the pressure has increased by the set amount (10 mmHg) and the speed of the left motor is then fixed at the present value.

After the calibration routine, the LAP is continuously monitored and the speed is adjusted to maintain the LAP within a set margin of that determined during the calibration procedure. The set margin may be for example 5 mmHg of the preset level, such that for any changes in pressure greater than 5 mmHg an adjustment to speed (RPM) of the left pump is made. The calibration routine may be periodically repeated, such as once a day.

Control of the right side motor may be performed using the calibration routine 300 to provide complete control of a rotary artificial heart. In at least one embodiment, the left side pump calibration is performed, and then the right side calibration is performed. During the calibration of one side, the speed of the other side may be kept constant to avoid any unstable behavior.

In a system using the control method described immediately above, the system is sensitive to and will adjust to accommodate physiologic changes that result in changes in aortic pressure (AOP) and RAP. When the AOP increases, the flow out of the left side pump will drop and the LAP will increase. The system will respond to the rise in LAP by increasing the speed of the left side pump to reduce the LAP. Similarly, a decrease in the AOP will result in increased flow, lower LAP, and subsequently an adjustment to reduce the speed of the left pump. When the RAP changes due to lower rate of return of blood to the right atria, the system will adjust speed of the right side pump to accommodate the change.

Figure 6A:
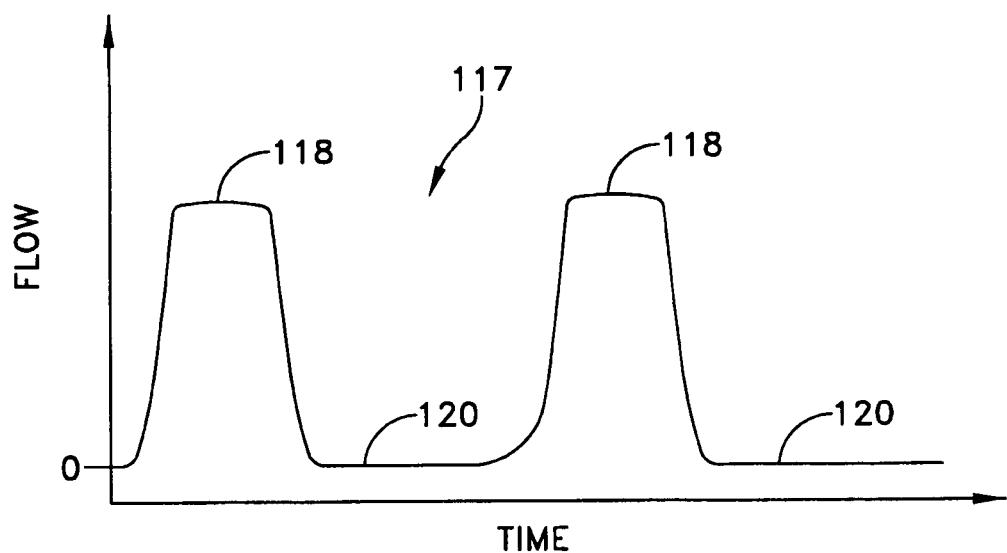
FIGS. 6A and 6B are representative plots of blood flow through rotary pumps in accordance with embodiments of the invention.
Figure 6B:
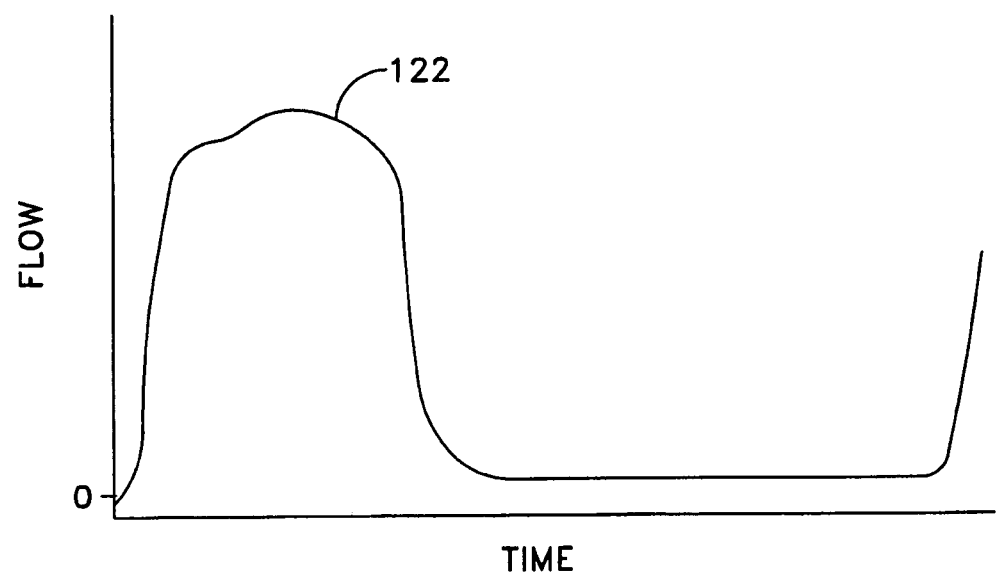
Figure 6C:
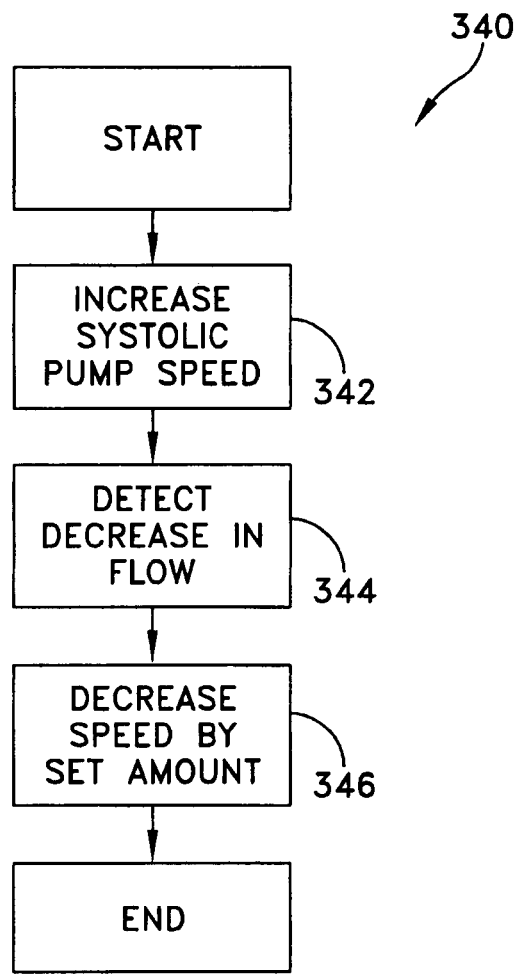
FIG. 6C is a flow chart of a process used in one embodiment of the invention.

In a fifth control scheme 340 in accordance with at least one embodiment, which will now be described with reference to FIGS. 6A, 6B and 6C pressure measurements are not used, and accordingly, pressure sensors need not be included in the artificial heart. In a rotary pump of an artificial heart operating in a pulsatile mode, the flow of blood through the rotary pump is pulsed on and off. As discussed above, the flow through a rotary pump may be determined based on the known speed and power of the pump. For an artificial heart operating in a steady-state mode, the flow may be somewhat constant and follow a curve 117 like that shown in FIG. 6A with the parts of the curve labeled 118 occurring when the pump is on at full speed (systole) and the parts labeled 120 occurring when the pump is on at a minimum speed (diastole, substantially no flow).

In the fifth control scheme, the speed of one or both pumps can be slowly increased during systole (stage 342), which may initially cause an increase in flow followed by a decrease in flow as the pressure in the atria drop. FIG. 6B shows one pulse 122 of blood flow through the left pump during systole with the speed of the pump being slowly increased during the systole period. The flow through the left pump increases with an increase in speed, and then the flow decreases as the volume of available blood in the left atrium decreases (and LAP decreases). In this control scheme, the decrease in flow is detected (stage 344), and the speed is then decreased by a set amount (stage 346) and set as the systolic speed of the pump. The control scheme allows the control module, based on power measurements, to adjust the speed to provide for maximum flow without undesirably allowing LAP or RAP to approach zero by detecting when draining of the atria is starting to occur. In one embodiment, the process for optimizing speed may be performed for both the right and left pumps on a continuous basis, while in other embodiments the process may be performed during alternating systolic periods for the left and right pumps to limit any interaction between the flows of the pumps during the adjustment process. Still, in other embodiments, the process may be performed less frequently than every other pulse.

In the fifth control scheme (or in any of the control schemes discussed above), the blood flow through the first pump may be compared with the blood flow through the second pump to ensure that the flow through the second pump is greater than the flow through the first pump to account for imbalances due to the bronchial shunt.

The fifth control scheme may be used in conjunction with control schemes one through four described above, as an additional layer of control to prevent LAP and/or RAP from approaching zero. One of control schemes one through four may be the primary control scheme for the pumps, with the control module continuously (or periodically) monitoring flow, and providing a reduction to speed (and/or set points) based on a detection of draining of one of the atrium. The process for monitoring flow described above to detect that LAP or RAP is approaching zero may be performed with embodiments having pumps that operate in a continuous mode as well as a pulsatile mode.

In control schemes described above in accordance with at least some embodiments, pressure sensors are used to determine LAP and RAP, which provide an indication of the blood level of the atrium (i.e., how full the atrium is). In other embodiments, other sensors may be used in place of the pressure sensors, including, for example, sensors that detect the size of the atrium and volume estimation sensors, such as ultrasonic sensors, sonomicrometry sensors, or electro-optic sensors, that can assess atrial volumes or overall size. Further, in other embodiments, blood oxygen meters and/or kinetic activity monitors may be used in embodiments of the present invention as sensing devices in control schemes of embodiments of the invention. Still further, in at least some embodiments, characteristics of motors of rotary pumps are monitored and controlled, such that the motors themselves effectively operate as sensors, allowing such embodiments to operate without pressure sensors or with less accurate pressure sensors.

In embodiments of control schemes of the present invention, the speed of rotary pumps is controlled to adjust the flow of blood through the pumps. In other embodiments, power may be controlled to cause changes in flow in response to detected parameters. Typically, when speed is increased, a rotary pump will draw more power, and when power is increased, the speed will be increased. Accordingly, in some embodiments, flow through rotary pumps may be increased by directly increasing speed (resulting in an increase in power draw) or flow may be increased by providing additional power (resulting in an increase in speed).

As discussed above, at least some control schemes of embodiments of the present invention may be used with totally artificial hearts intended to replace a natural heart, with implantable ventricular assist devices and with external blood pumps. Further, at least some of the control schemes described above provide proper physiologic blood flow to allow the average blood flow of the left pump to be greater than the average blood flow of the right pump.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of controlling a dual rotary blood pump having a first pump comprising a first impeller in contact with and configured to pump blood to a patient's lungs and a second pump comprising a second impeller in contact with and configured to pump blood to the patient's body, the method comprising:
   detecting, the patient's left atrial pressure;
   detecting the patient's right atrial pressure; and
   controlling operation of the first pump and the second pump based on the left atrial pressure and the right atrial pressure to maintain blood flow in the body such that an average flow of blood through the second pump is greater than an average flow of blood through the first pump,
   wherein the method further includes setting a target pressure level for the left atrial pressure based on a speed of the second pump at which the left atrial pressure approaches a threshold value.

2. The method of claim 1, further comprising adjusting the speed of the second pump based on changes in the left atrial pressure from the target pressure level.

3. The method of claim 2, further comprising setting a target pressure level of the right atrial pressure based on a speed of the first pump at which the right atrial pressure approaches a threshold value.

4. The method of claim 1, further comprising controlling each of the first pump and the second pump to operate in a pulsatile mode of operation.

5. The method of claim 1, further comprising determining blood flow through at least one of the first pump and the second pump by dithering at least one of speed and power usage of the at least one of the first pump and the second pump.

6. A method of controlling a dual rotary blood pump having a first rotary pump comprising a first impeller in contact with and configured to pump blood to a patient's lungs and a second rotary pump comprising a second impeller in contact with and configured to pump blood to the patient's body, the method comprising:
   determining a first blood flow rate through the first rotary pump;
   determining a second blood flow rate through the second rotary pump;
   controlling the first rotary pump and the second rotary pump based on the first blood flow rate and the second blood flow rate to maintain a difference between the first blood flow rate and the second blood flow rate; and
   increasing a rotational speed of the second rotary blood pump until a drop in the second blood flow rate is detected.

7. The method of claim 6, wherein determining the first blood flow rate includes dithering at least one of speed and power usage of the first rotary pump.

8. A method of controlling a dual rotary blood pump having a first rotary pump comprising a first impeller in contact with and configured to pump blood to a patient's lungs and a second rotary pump comprising a second impeller in contact with and configured to pump blood to the patient's body, the method comprising:
 determining a first blood flow rate through the first rotary pump;
 determining a second blood flow rate through the second rotary pump;
 controlling the first rotary pump and the second rotary pump based on the first blood flow rate and the second blood flow rate to maintain a difference between the first blood flow rate and the second blood flow rate; and
 increasing a rotational speed of the first rotary blood pump until a drop in the first blood flow rate is detected.

9. A method of controlling a dual rotary blood pump having a first rotary pump comprising a first impeller in contact with and configured to pump blood to a patient's lungs and a second rotary pump comprising a second impeller in contact with and configured to pump blood to the patient's body, the method comprising:
 determining a first blood flow rate through the first rotary pump;
 determining a second blood flow rate through the second rotary pump; and
 controlling the first rotary pump and the second rotary pump based on the first blood flow rate and the second blood flow rate to maintain a difference between the first blood flow rate and the second blood flow rate, wherein determining the second blood flow rate includes dithering at least one of speed and power usage of the second rotary pump.

* * * * *

UNITED STATES PATENT AND TRADEMARK OFFICE
CERTIFICATE OF CORRECTION

| | | |
|---|---|---|
| PATENT NO. | : 8,657,875 B2 | Page 1 of 1 |
| APPLICATION NO. | : 11/235691 | |
| DATED | : February 25, 2014 | |
| INVENTOR(S) | : Kung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 752 days.

Signed and Sealed this
Twenty-second Day of March, 2016

Michelle K. Lee
*Director of the United States Patent and Trademark Office*